United States Patent
DiPietro et al.

(10) Patent No.: US 7,465,837 B2
(45) Date of Patent: *Dec. 16, 2008

(54) FLUORINATED VINYL ETHERS, COPOLYMERS THEREOF, AND USE IN LITHOGRAPHIC PHOTORESIST COMPOSITIONS

(75) Inventors: Richard A. DiPietro, Campbell, CA (US); Hiroshi Ito, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/503,356

(22) Filed: Aug. 10, 2006

(65) Prior Publication Data

US 2006/0287558 A1    Dec. 21, 2006

Related U.S. Application Data

(63) Continuation of application No. 10/424,673, filed on Apr. 25, 2003, now Pat. No. 7,150,957.

(51) Int. Cl.
  *C07C 41/00*    (2006.01)
(52) U.S. Cl. .................. 568/615; 568/616; 568/649; 568/674; 568/685
(58) Field of Classification Search ............ 568/615, 568/616, 649, 674, 685
See application file for complete search history.

(56) References Cited

U.S. PATENT DOCUMENTS

| | | | |
|---|---|---|---|
| 4,513,128 A | 4/1985 | Uschold | |
| 6,232,417 B1 | 5/2001 | Rhodes et al. | |
| 6,468,712 B1 | 10/2002 | Fedynyshyn | |
| 6,509,134 B2 | 1/2003 | Ito et al. | |
| 6,548,219 B2 | 4/2003 | Ito et al. | |
| 6,593,058 B1 * | 7/2003 | Feiring et al. ............ | 430/270.1 |

(Continued)

FOREIGN PATENT DOCUMENTS

JP    2002220416    *    8/2002

OTHER PUBLICATIONS

Abstract of Jp 2002220416. Aug. 9, 2002.*

(Continued)

*Primary Examiner*—Hoa V Le
(74) *Attorney, Agent, or Firm*—Isaac M. Rutenberg; Mintz, Levin, Cohn, Ferris, Glovsky, and Popeo P.C.

(57) ABSTRACT

Fluorinated vinyl ethers are provided having the structure of formula (I) the structure of formula (I)

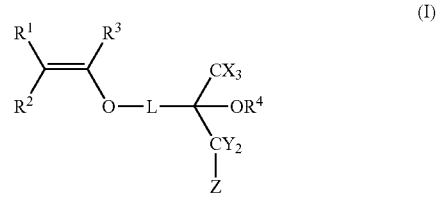

wherein at least one of X and Y is a fluorine atom, and L, $R^1$, $R^2$, $R^3$, $R^4$ are as defined herein. Also provided are copolymers prepared by radical polymerization of (I) and a second monomer that may not be fluorinated. The polymers are useful in lithographic photoresist compositions, particularly chemical amplification resists. In a preferred embodiment, the polymers are substantially transparent to deep ultraviolet (DUV) radiation, and are thus useful in DUV lithographic photoresist compositions. A method for using the composition to generate resist images on a substrate is also provided, i.e., in the manufacture of integrated circuits or the like.

1 Claim, 3 Drawing Sheets

U.S. PATENT DOCUMENTS

| | | | |
|---|---|---|---|
| 6,908,724 B2* | 6/2005 | Araki et al. | 430/270.1 |
| 7,150,957 B2* | 12/2006 | DiPietro et al. | 430/281.1 |
| 2002/0048724 A1 | 4/2002 | Harada et al. | |
| 2002/0051936 A1 | 5/2002 | Harada et al. | |
| 2002/0058199 A1 | 5/2002 | Zampini et al. | |
| 2002/0146639 A1 | 10/2002 | Brock et al. | |
| 2002/0160297 A1 | 10/2002 | Fedynyshyn et al. | |
| 2002/0160303 A1* | 10/2002 | Kim et al. | 430/270.1 |
| 2002/0164538 A1 | 11/2002 | Allen et al. | |
| 2003/0091928 A1* | 5/2003 | Choi | 430/270.1 |
| 2003/0211417 A1* | 11/2003 | Fryd et al. | 430/270.1 |
| 2003/0235781 A1* | 12/2003 | Shida et al. | 430/270.1 |

OTHER PUBLICATIONS

Machine English language translation of Jp 2002220416. Aug. 9, 2002.*

U.S. Appl. No. 10/090,646, filed Sep. 11, 2003, Breyta et al.

U.S. Appl. No. 10/091,373, filed Oct. 2, 2003, Ito.

Choi et al., (2000) "Design and Synthesis of New Materials for ArF Lithography," in *Advances in Resist Technology*, F. Houlihan, Ed., Proceedings of SPIE 3999.

Fujigaya et al., (2002) "A New Photoresist Material for 157 nm Lithography-2," *Journal of Photopolymer Science and Technology*, 15(4):643-654.

Ito et al. (1982), "Polymerization of Methyl $\alpha$-(Trifluoromethyl)acrylate and $\alpha$-(Trifluoromethyl)acrylonitrile and Copolymerization of These Monomers with Methyl Methacrylate," *Macromolecules* 15:915.

Ito et al. (1984), "Radical Reactivity and Q-e Values of Methyl $\alpha$-(Trifluoromethyl)-acrylate," *Macromolecules* 17:2204.

Ito et al. (1987), "Anionic Polymerization of $\alpha$-(Trifluoromethyl)Acrylate," in *Recent Advances in Anionic Polymerization*, T. E. Hogen-Esch and J. Smid, Eds. (Elsevier Science Publishing Co., Inc.).

Kunz et al., "Outlook for 157-nm Resist Design," SPIE Conference on Advances in Resist Technology and Processing XVI, Santa Clara, CA (Mar. 1999).

Okimoto et al. (2002), "Development of a Highly Efficient Catalytic Method for Synthesis of Vinyl Ethers," *J. Am. Chem. Soc.* 124(8):1590-1591.

Watanabe et al. (1957), "Homogenous Metal Salt Catalysis in Organic Reactions. I. The Preparation of Vinyl Ethers by Vinyl Transetherification,"*J. Am. Chem. Soc.* 79:2828-2833.

Willison et al. (1983), "Poly(methyl $\alpha$-Trifluoromethylacrylate) as a Positive Electron Beam Resist," *Polymer Engineering and Science* 23(18):1000-1003.

* cited by examiner

500nm

500nm

FLUORINATED VINYL ETHERS, COPOLYMERS THEREOF, AND USE IN LITHOGRAPHIC PHOTORESIST COMPOSITIONS

CROSS-REFERENCE TO RELATED APPLICATIONS

This is a continuation of U.S. patent application Ser. No. 10/424,673, filed Apr. 25, 2003, the disclosure of which is incorporated by reference in its entirety.

TECHNICAL FIELD

This invention relates generally to the fields of polymer chemistry, lithography, and semiconductor fabrication. More specifically, the invention relates to novel monomers capable of undergoing radical copolymerization with electron-deficient monomers, to form a copolymer suitable for use in a lithographic photoresist ("resist") composition, particularly in a chemical amplification photoresist composition, e.g., a deep-ultraviolet (DUV) photoresist composition.

BACKGROUND OF THE INVENTION

Ongoing efforts are being made in the field of microelectronic devices to achieve a higher circuit density. One method of increasing the number of components per chip is to decrease the minimum feature size on the chip, which requires higher lithographic resolution. This was accomplished over the years by reducing the wavelength of the imaging radiation from the visible (436 nm) down through the ultraviolet (365 nm) to the deep ultraviolet (DUV) at 248 nm. Development of commercial lithographic processes using ultra-deep ultraviolet radiation, particularly 193 nm and 157 nm, has become of significant interest. See, with respect to 193 nm resists, Allen et al. (1995), "Resolution and Etch Resistance of a Family of 193 nm Positive Resists," *J. Photopolym. Sci. and Tech.* 8(4):623, and Abe et al. (1995), "Study of ArF Resist Material in Terms of Transparency and Dry Etch Resistance," *J. Photopolym. Sci. and Tech* 8(4):637.

In order for photoresists to function properly, their films must be transparent enough at the exposing wavelength to enable sufficient light to penetrate to the bottom of the film to create usable developed relief images. This generally corresponds to a maximum absorbance of up to approximately 0.4 or 0.5 for the required film thickness. The poor transparency at 157 nm of the polymers currently used in 248 nm (primarily p-hydroxystyrene based) and 193 nm resists (polymethacrylates and norbornene-maleic anhydride co- and terpolymers) is well known and there is some level of understanding of what types of polymers are transparent at 157 nm. See Kunz et al. (1999), "Outlook for 157 nm Resist Design," *Proc. SPIE* 3678, 13. The most transparent materials identified to date, heavily fluorinated polymers such as polytetrafluoroethylene (e.g., Teflon AF®; see Endert et al. (1999) *Proc. SPIE-Int. Soc. Opt. Eng,* 3618:413) or hydridosilsesquioxanes (see U.S. Pat. No. 6,087,064 to Lin et al.), are not suitable because they do not have the requisite reactivity or solubility characteristics. The challenge in developing chemically amplified resists for 157 nm lithography is in achieving suitable transparency in polymers that can be developed efficiently using industry standard developers.

Homo- and copolymers of methyl α-trifluoromethylacrylate (MTFMA) have been found to be surprisingly transparent at 157 nm, exhibiting an optical density (OD) of 3/μm, while poly(methyl methacrylate) (PMMA) is highly absorbing (exhibiting an OD of 5.7/μm at 157 nm). Unfortunately, however, MTFMA is reluctant to undergo radical homopolymerization and homopolymer can be made only by anionic polymerization. Its incorporation into copolymers with methacrylates is significantly less than 50%. See Ito et al. (1981), "Methyl Alpha-Trifluoromethylacrylate, an E-Beam and UV Resist," *IBM Technical Disclosure Bulletin* 24(4):991; Ito et al. (1982), "Polymerization of Methyl α-(Trifluoromethyl)acrylate and α-(Trifluoromethyl)-acrylonitrile and Copolymerization of These Monomers with Methyl Methacrylate," *Macromolecules* 15:915; Willson et al. (1983), "Poly(methyl α-Trifluoromethylacrylate) as a Positive Electron Beam Resist," *Polymer Engineering and Science* 23(18):1000-1003; Ito et al. (1984) "Radical Reactivity and Q-e Values of Methyl α-(Trifluoromethyl)acrylate," *Macromolecules* 17:2204; and Ito et al. (1987), "Anionic Polymerization of α-(Trifluoromethyl)Acrylate," in *Recent Advances in Anionic Polymerization*, T. E. Hogen-Esch and J. Smid, Eds. (Elsevier Science Publishing Co., Inc.).

Certain norbornene derivatives have been identified as comonomers that undergo radical copolymerization with α-trifluoromethylacrylic monomers, as described in U.S. Pat. No. 6,509,134 to Ito et al. and in U.S. Patent Application Publication No. 2002/0102490 A1. In addition, it has been demonstrated, quite recently, that MTFMA and other α-trifluoromethylacrylic esters undergo radical copolymerization with various vinyl ether derivatives, which has opened up more possibilities in the design of 157 nm and 193 nm bilayer and single layer resist materials; see, e.g., U.S. patent application Ser. No. 10/091,373 to Ito, filed Mar. 4, 2002, for "Copolymer for Use in Amplification Resists," assigned to International Business Machines Corporation. Vinyl ethers have been copolymerized with maleic anhydride (MA) for the design of 193 nm resists, as described by Choi et al. (2000), "Design and Synthesis of New Photoresist Materials for ArF Lithography," *Proc. SPIE* 3999:54. A third functional monomer, however, had to be terpolymerized with the vinyl ether and MA because neither the vinyl ether used nor the MA was functionalized. In addition, incorporation of a conventional vinyl ether into a copolymer does not increase the polymer's polarity, and so does not enhance the efficiency of resist development in industry standard developers. Furthermore, conventional vinyl ethers do not enhance the 157 nm transparency of a copolymer containing an α-trifluoromethylacrylate co-monomer.

There is, accordingly, a need in the art for new polymers that exhibit enhanced transparency at 157 nm and contain a sufficient number of polar groups so that solubility in industry standard developers, particularly aqueous base, is improved relative to the solubility of previously disclosed polymers used in 157 nm resists.

SUMMARY OF THE INVENTION

In one aspect of the invention, then, a fluorinated vinyl ether is provided that is capable of undergoing radical polymerization with a second monomer, e.g., an electron-deficient monomer, to give a copolymer exhibiting good transparency in the DUV and enhanced solubility in industry standard developers, particularly in aqueous base. The fluorinated vinyl ether is composed of ethylene directly substituted on an olefinic carbon atom with a moiety —OR* and optionally further substituted on an olefinic carbon atom with one, two, or three additional nonhydrogen substituents, wherein R* comprises a fluorinated alkyl moiety substituted with a protected or unprotected hydroxyl group, and further wherein an atom within R* may be (a) taken together with one of the additional nonhydrogen substituents, if present, or (b) directly bound to an olefinic carbon atom, to form a ring.

In one embodiment, R* has the structure -L-C(CX$_3$)(CY$_2$Z)(OR$^4$), such that the fluorinated vinyl ether has the structure of formula (I)

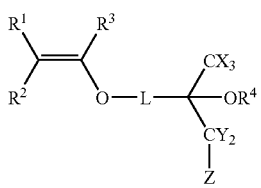

wherein:

L is selected from C$_1$-C$_{12}$ alkylene, substituted C$_1$-C$_{12}$ alkylene (e.g., C$_1$-C$_{12}$ fluoroalkylene), C$_1$-C$_{12}$ heteroalkylene, substituted C$_1$-C$_{12}$ heteroalkylene, C$_3$-C$_{15}$ alicyclic, C$_3$-C$_{15}$ fluoroalicyclic, C$_5$-C$_{14}$ aryl, substituted C$_5$-C$_{14}$ arylene (e.g., C$_5$-C$_{14}$ fluoroarylene), C$_5$-C$_{14}$ heteroarylene, substituted C$_5$-C$_{14}$ heteroarylene, and combinations thereof;

X is H or F;

Y is H or F, providing that when X is H, then Y is F;

Z is identical to Y, or is taken together with another substituent to form a ring;

R$^1$ is selected from H, C$_1$-C$_{12}$ alkyl, fluorinated C$_{1-12}$ alkyl, and C$_3$-C$_{15}$ alicyclic;

R$^2$ is selected from H, C$_1$-C$_{12}$ alkyl, fluorinated C$_{1-12}$ alkyl, and C$_3$-C$_{15}$ alicyclic, or R$^2$ and one of L and Z are taken together to form a ring, generally a five-membered to nine-membered ring; and R$^3$ is selected from H, C$_1$-C$_{12}$ alkyl, and C$_3$-C$_{15}$ alicyclic, or R$^3$ and one of R$^1$, L, and Z are taken together to form a ring, generally a five-membered to nine-membered ring;

R$^4$ is selected from H, an acid-labile group optionally substituted with one or more fluorine atoms, and an acid-inert moiety optionally substituted with one or more fluorine atoms.

In another aspect of the invention, a copolymer is provided that is prepared by copolymerization of a fluorinated vinyl ether as described above, e.g., a fluorinated vinyl ether having the structure of formula (I), with a second monomer having the structure of formula (II)

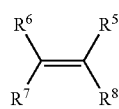

wherein:

R$^5$ is selected from F, lower fluoroalkyl, cyano, —(CO)—O—R$^9$, —(CO)—NR$^{10}$R$^{11}$, —(CO)—R$^{12}$, and —S(O)$_2$—OR$^{13}$, or is taken together with R$^6$ or R$^8$ to form a ring, generally a five- to nine-membered ring;

R$^6$, R$^7$, and R$^8$ are independently selected from H, F, lower alkyl, lower fluoroalkyl, cyano, —(CO)—O—R$^9$, —(CO)—NR$^{10}$R$^{11}$, —(CO)—R$^{12}$, and —S(O)$_2$—OR$^{13}$, or wherein R$^7$ is taken together with R$^6$ or R$^8$ to form a ring, generally a five- to nine-membered ring;

R$^9$ is H, an acid-labile moiety optionally substituted with one or more fluorine atoms, or an acid-inert moiety optionally substituted with one or more fluorine atoms; and R$^{10}$, R$^{11}$, R$^{12}$, and R$^{13}$ are independently selected from H, C$_1$-C$_{12}$ alkyl, substituted C$_1$-C$_{12}$ alkyl, C$_1$-C$_{12}$ heteroalkyl, substituted C$_1$-C$_{12}$ heteroalkyl, C$_3$-C$_{15}$ alicyclic, C$_3$-C$_{15}$ fluoroalicyclic, C$_5$-C$_{14}$ aryl, substituted C$_5$-C$_{14}$ aryl, C$_5$-C$_{14}$ heteroaryl, and substituted C$_5$-C$_{14}$ heteroarylene.

The copolymers may be blended with one or more additional polymers, with any such additional polymers generally selected to increase transparency at a desired wavelength, increase dry etch resistance, and/or improve aqueous base development. Representative additional polymers are disclosed in U.S. patent application Ser. No. 10/090,646 to Breyta et al., filed Mar. 4, 2002, for "Polymer Blend and Associated Methods of Preparation and Use," assigned to International Business Machines Corporation. A preferred additional polymer contains monomer units bearing a fluoroalcohol group, such as NBHFA (bicyclo[2.2.1]hept-5-ene-2-(1,1,1-trifluoro-2-trifluoromethylpropan-2-ol). These preferred polymers may be NBHFA homopolymers ("PNBHFA") or copolymers of NBHFA with other monomers, including, without limitation, other norbornene monomers. Copolymer blends of the invention are not limited in this respect, however, and the invention encompasses blends of the present copolymers with any suitable polymers.

These copolymers have excellent transparency in the DUV, e.g., exhibiting an OD that is less than 2.5, preferably less than 2.0, or even less than 1.5 at 157 nm, depending on the comonomer. The copolymers also have a lower and controllable glass transition temperature T$_g$, in turn providing better adhesion and the possibility of annealing to achieve better environmental stability.

In an additional aspect of the invention, the aforementioned copolymer is incorporated into a photoresist along with a radiation-sensitive acid generator. The photoresist so provided will generally, although not necessarily, contain a dissolution modifying additive (e.g., a dissolution inhibitor), a solvent, and at least one additive selected from dyes, sensitizers, stabilizers, acid diffusion controlling agents, surfactants, anti-foaming agents, adhesion promoters, and plasticizers. The photoresist is used in a process for generating a resist image on a substrate by: (a) coating a substrate with a film of the photoresist; (b) exposing the film selectively to a predetermined pattern of radiation so as to form a latent, patterned image in the film; and (c) developing the latent image with a developer. The radiation may be electron-beam, x-ray, or ultraviolet radiation, although radiation in the DUV, particularly radiation having a wavelength of 157 nm, is preferred. The photoresist provides higher resolution and better performance than previous polymers proposed for use in 157 nm resists.

The invention additionally pertains to a method of forming a patterned material structure on a substrate by: (a) applying a photoresist composition of the invention to a substrate surface to form a resist layer over a material selected from a semiconductor, a ceramic, and a metal; (b) patternwise exposing the resist to radiation whereby acid is generated by the radiation-sensitive acid generator in exposed regions of the resist layer; (c) contacting the resist with a developer solution, whereby the developed regions of the resist layer reveal a patterned resist structure; and (d) transferring the resist structure pattern to the material by etching into said material through spaces in the resist structure.

The disclosure provides a fluorinated vinyl ether having the structure

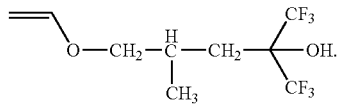

DETAILED DESCRIPTION OF THE INVENTION

I. Definitions and Nomenclature

Figure 1A:
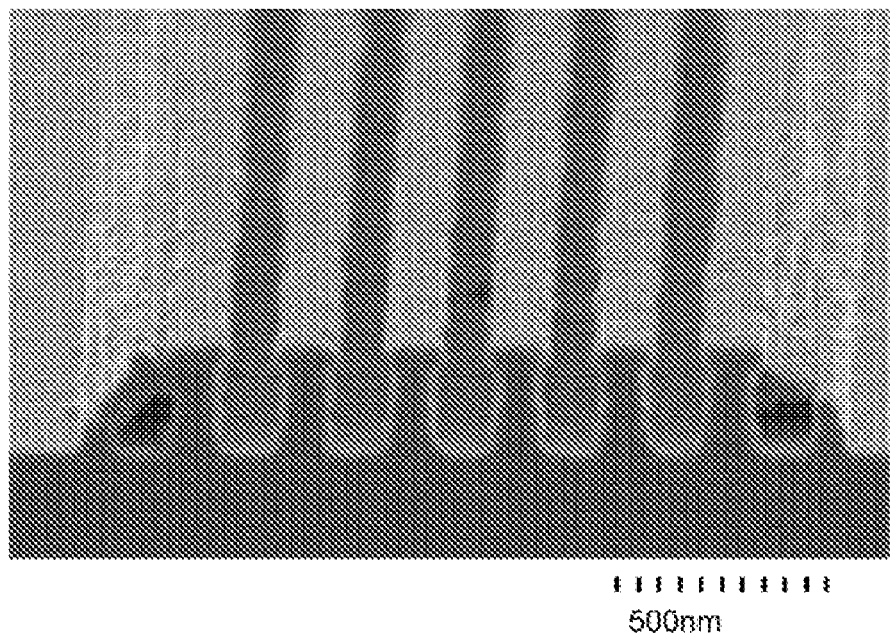
FIGS. 1A and 1B are SEM photos of the patterned resist prepared as described in Example 11, using a 193 nm exposure step.

Unless otherwise indicated, this invention is not limited to specific compositions, components, or process steps. It should also be noted that the singular forms "a" and "the" are intended to encompass plural referents, unless the context clearly dictates otherwise. The terminology used herein is for the purpose of describing particular embodiments only and is not intended to be limiting.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear or branched, saturated hydrocarbon substituent that generally, although not necessarily, contains 1 to about 24 carbon atoms, such as methyl, ethyl, n-propyl, isopropyl, n-butyl, isobutyl, t-butyl, octyl, decyl, tetradecyl, hexadecyl, eicosyl, tetracosyl, and the like. Generally, although again not necessarily, alkyl groups herein contain 1 to about 12 carbon atoms. The term "lower alkyl" intends an alkyl group of 1 to 6 carbon atoms, and the term "cycloalkyl" intends a cyclic alkyl group, typically having 3 to 8, preferably 3 to 7, carbon atoms. The term "substituted alkyl" refers to alkyl substituted with one or more substituent groups, i.e., wherein a hydrogen atom is replaced with a non-hydrogen substituent group, and the terms "heteroatom-containing alkyl" and "heteroalkyl" refer to alkyl substituents in which at least one carbon atom is replaced with a heteroatom such as O, N, or S. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear or branched saturated hydrocarbon linkage, typically although not necessarily containing 1 to about 24 carbon atoms, such as methylene, ethylene, n-propylene, n-butylene, n-hexylene, decylene, tetradecylene, hexadecylene, and the like. Preferred alkylene linkages contain 1 to about 12 carbon atoms, and the term "lower alkylene" refers to an alkylene linkage of 1 to 6 carbon atoms, preferably 1 to 4 carbon atoms. The term "substituted alkylene" refers to an alkylene linkage substituted with one or more substituent groups, i.e., wherein a hydrogen atom is replaced with a non-hydrogen substituent group, and the terms "heteroatom-containing alkylene" and "heteroalkylene" refer to alkylene linkages in which at least one carbon atom is replaced with a heteroatom. If not otherwise indicated, the terms "alkylene" and "lower alkylene" include linear, branched, cyclic, unsubstituted, substituted, and/or heteroatom-containing alkylene and lower alkylene, respectively.

The term "alkoxy" as used herein refers to a group —O-alkyl wherein "alkyl" is as defined above.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms and either one aromatic ring or 2 to 4 fused or linked aromatic rings, e.g., phenyl, naphthyl, biphenyl, and the like, with more preferred aryl groups containing 1 to 3 aromatic rings, and particularly preferred aryl groups containing 1 or 2 aromatic rings and 5 to 14 carbon atoms. "Substituted aryl" refers to an aryl moiety substituted with one or more substituent groups, and the terms "heteroatom-containing aryl" and "heteroaryl" refer to an aryl group in which at least one ring carbon atom is replaced with a heteroatom. Unless otherwise indicated, the term "aryl" includes substituted and/or heteroaryl species.

The term "arylene" as used herein refers to an aromatic linkage defined as for "aryl" substituents above, but wherein the aryl moiety is bifunctional instead of monofunctional. Unless otherwise indicated, the term "arylene" includes substituted and/or heteroarylene species.

The term "alicyclic" is used to refer to cyclic, non-aromatic compounds, substituents and linkages, e.g., cycloalkanes and cycloalkenes, cycloalkyl and cycloalkenyl substituents, and cycloalkylene and cycloalkenylene linkages. Often, the term refers to bridged bicyclic compounds, substituents, and linkages. Preferred alicyclic moieties herein contain 3 to about 15 carbon atoms. Unless otherwise indicated, the term "alicyclic" includes substituted and/or heteroatom-containing such moieties.

The term "fluorinated" refers to replacement of a hydrogen atom in a molecule or molecular segment with a fluorine atom, and includes perfluorinated moieties. The term "perfluorinated" is also used in its conventional sense to refer to a molecule or molecular segment wherein all hydrogen atoms are replaced with fluorine atoms. Thus, a "fluorinated" methyl group encompasses —$CH_2F$ and —$CHF_2$ as well as the "perfluorinated" methyl group, i.e., —$CF_3$ (trifluoromethyl). The term "fluoroalkyl" refers to a fluorinated alkyl group, the term "fluoroalkylene" refers to a fluorinated alkylene linkage, the term "fluoroaryl" refers to a fluorinated aryl substituent, the term "fluoroarylene" refers to a fluorinated arylene linkage, the term "fluoroalicyclic" refers to a fluorinated alicyclic moiety, and the like.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with a non-hydrogen substituent. Examples of such substituents include, without limitation, functional groups such as halide, hydroxyl, alkoxy, acyl (including alkylcarbonyl (—CO-alkyl) and arylcarbonyl (—CO-aryl)), acyloxy (—O-acyl), alkoxycarbonyl (—(CO)—O-alkyl), aryloxycarbonyl (—(CO)—O-aryl), and silyl (e.g., trialkylsilyl), and hydrocarbyl moieties such as alkyl, aryl, aralkyl (aryl-substituted alkyl), and alkaryl (alkyl-substituted aryl). The aforementioned functional groups may, if a particular group permits, be further substituted with one or more additional functional groups or with one or more hydrocarbyl moieties such as those specifically enumerated above, and analogously, the above-mentioned hydrocarbyl moieties may be further substituted with one or more functional groups or additional hydrocarbyl moieties such as those specifically enumerated.

The term "polymer" is used to refer to a chemical compound that comprises linked monomers, and that may be linear, branched, or crosslinked. The term also encompasses not only homopolymers, but also copolymers, terpolymers, and the like. The term "copolymer," unless specifically indicated otherwise, refers to a polymer containing at least two different monomer units.

When two substituents are indicated as being "taken together to form a ring," several possibilities are encompassed. That is, when R and R' of the following hypothetical compound are indicated as being taken together to form a ring

the resulting compounds include (1) those wherein a single spacer atom links the carbon atoms indicated at * and ** (i.e., R and R' "taken together" together form a single atom that may or may not be substituted, e.g., $CH_2$ or O), (2) those wherein a direct covalent bond is formed between R and R', and (3) those wherein R and R' are linked through a bifunctional moiety containing one or more spacer atoms, as respectively illustrated in the following structures.

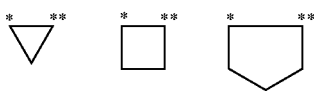

In addition, compounds in which R and R' are "taken together to form a ring" include compounds in which the linked atoms are not necessarily contained within a terminal group. For example, when R of the above formula is $-CH_2CH_3$ and R' is $-CH_2CF_3$, such that the compound has the structure

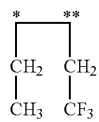

then compounds in which R and R' are taken together to form a ring include both

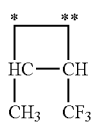 and 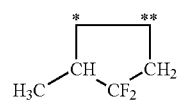

The term "ring" is intended to include all types of cyclic groups, although the rings of primary interest herein are alicyclic, including cycloalkyl and substituted and/or heteroatom-containing cycloalkyl, whether monocyclic, bicyclic (including bridged bicyclic), or polycyclic. Preferred rings are substituted and/or heteroatom-containing monocyclic rings.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "acid-labile" refers to a molecular segment containing at least one covalent bond that is cleaved upon exposure to acid.

Analogously, the term "acid-inert" refers to a substituent that is not cleaved or otherwise chemically modified upon contact with photogenerated acid.

The terms "photogenerated acid" and "photoacid" are used interchangeably herein to refer to the acid that is created upon exposure of the present compositions to radiation, i.e., as a result of the radiation-sensitive acid generator in the compositions.

The term "substantially transparent" as used to describe a polymer that is "substantially transparent" to radiation of a particular wavelength refers to a polymer that has an absorbance of less than about 5.0/micron, preferably less than about 4.0/micron, most preferably less than about 3.5/micron, at a selected wavelength.

For additional information concerning terms used in the field of lithography and lithographic compositions, see *Introduction to Microlithography*, Eds. Thompson et al. (Washington, D.C.: American Chemical Society, 1994).

II. The Fluorinated Vinyl Ethers and Copolymers Thereof

The fluorinated vinyl ether monomers of the invention used to prepare copolymers for incorporation into lithographic photoresists are composed of ethylene directly substituted on an olefinic carbon atom with a moiety —OR* and optionally further substituted on an olefinic carbon atom with one, two, or three additional nonhydrogen substituents, wherein R* comprises a fluorinated alkyl moiety substituted with a protected or unprotected hydroxyl group, and further wherein an atom within R* may be (a) taken together with one of the additional nonhydrogen substituents, if present, or (b) directly bound to an olefinic carbon atom, to form a ring.

In a preferred embodiment, R* has the structure -L-C(CX$_3$)(CY$_2$Z)(OR$^4$), such that the fluorinated vinyl ether has the structure of formula (I)

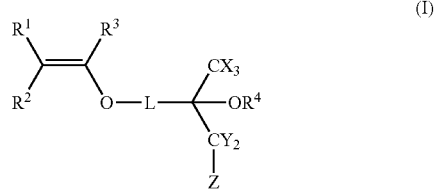

wherein the various substituents are as follows.

The linker L is selected from $C_1$-$C_{12}$ alkylene, substituted $C_1$-$C_{12}$ alkylene (e.g., $C_1$-$C_{12}$ fluoroalkylene), $C_1$-$C_{12}$ heteroalkylene, substituted $C_1$-$C_{12}$ heteroalkylene, $C_3$-$C_{15}$ alicyclic, $C_3$-$C_{15}$ fluoroalicyclic, $C_5$-$C_{14}$ aryl, substituted $C_5$-$C_{14}$ arylene (e.g., $C_5$-$C_{14}$ fluoroarylene), $C_5$-$C_{14}$ heteroarylene, and substituted $C_5$-$C_{14}$ heteroarylene, or may be comprised of a combination of two or more of the aforementioned linkages. Preferred L moieties include, without limitation, $C_1$-$C_{12}$ alkylene, $C_1$-$C_{12}$ fluoroalkylene, $C_3$-$C_{15}$ alicyclic, $C_3$-$C_{15}$ fluoroalicyclic, $C_5$-$C_{14}$ arylene, $C_5$-$C_{14}$ fluoroarylene, and combinations thereof. In a more preferred embodiment, L is $C_1$-$C_{12}$ alkylene, $C_3$-$C_{15}$ alicyclic, or a combination thereof. For example, L may be —(CH$_2$)$_3$—, —CH$_2$—CH(CH$_3$)—CH$_2$—, —(CH$_2$)$_4$—, —(CH$_2$)$_5$—, norbornanyl (NB), adamantanyl (AD), —NB—CH$_2$—, etc.

X is H or F, and Y is H or F, providing that when X is H, then Y is F. Z is identical to Y, or is taken together with another substituent to form a ring, as described infra. In the latter case, the carbon atom to which Z is attached—as well as Z per se—may be directly bound to either olefinic carbon atom in order to form a ring. Analogously, a ring may be formed when the carbon atom to which the Y substituents are attached is directly bound to one of the olefinic carbon atoms.

$R^1$ is selected from: H; $C_1$-$C_{12}$ alkyl, preferably lower alkyl; fluorinated $C_{1-12}$ alkyl; and $C_3$-$C_{15}$ alicyclic. In a particularly preferred embodiment, $R^1$ is H.

$R^2$ is also selected from: H; $C_1$-$C_{12}$ alkyl, preferably lower alkyl; fluorinated $C_{1-12}$ alkyl, and $C_3$-$C_{15}$ alicyclic. $R^2$, however, may also be taken together with either L or Z to form a ring, e.g., a five-membered to nine-membered ring, as will be described infra. In a particularly preferred embodiment, $R^2$ is H.

$R^3$ is selected from H, $C_1$-$C_{12}$ alkyl, and $C_3$-$C_{15}$ alicyclic, or $R^3$ and one of $R^1$, L, and Z are taken together to form a ring, e.g., a five-membered to nine-membered ring. In a preferred embodiment, $R^3$ is H or $C_1$-$C_{12}$ alkyl, more preferably H or lower alkyl, most preferably H.

When $R^1$ and $R^3$ are taken together to form a ring, $R^2$ is preferably H. In this case, there is a linkage between $R^1$ and $R^3$ that typically contains three to seven spacer atoms, preferably three to five spacer atoms, which is generally alkylene or substituted and/or heteroatom-containing alkylene. As an example, when $R^1$ and $R^3$ are linked through an unsubstituted alkylene chain, the fluorinated vinyl ether has the structure of formula (III)

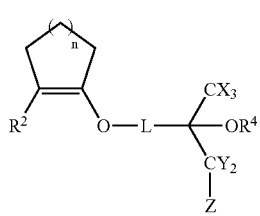

(III)

wherein n is preferably 1, 2, 3, 4, or 5 and L, X, Y, Z, $R^2$, and $R^4$ are as defined previously. When the ring formed between $R^1$ and $R^3$ is five- to seven-membered, n is then 1, 2, or 3.

When $R^2$ and L are taken together to form a ring, $R^1$ and $R^3$ are preferably although not necessarily H. Generally, the ring is a five- to nine-membered ring, preferably a five- to seven-membered ring, which is generally a cycloalkyl ring that is optionally substituted and/or heteroatom-containing. One such group of compounds is represented by the structure of formula (IV)

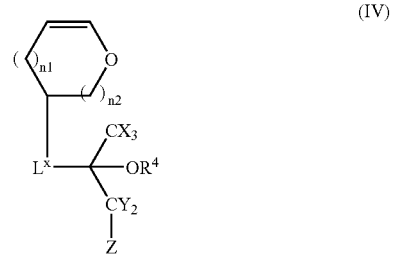

(IV)

wherein X, Y, Z, and $R^4$ are as defined previously, n1 and n2 are integers in the range of zero to 5, the sum of n1 and n2 is in the range of 1 to 5, preferably in the range of 1 to 3, and $L^x$ is a direct bond or represents a terminal segment of L extending from the carbon atom within L that is bound to $R^2$.

Analogously, when $R^3$ and L are taken together to form a ring, typically a five- to nine-membered ring, preferably a five- to seven-membered ring, which is generally a cycloalkyl ring that is optionally substituted and/or heteroatom-containing, then $R^1$ and $R^2$ are preferably although not necessarily H. One group of such structures, when the linkage is unsubstituted alkylene, is represented by formula (V)

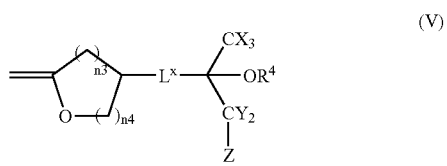

(V)

wherein X, Y, Z, and $R^4$ are as defined previously, n3 and n4 are integers in the range of zero to 5, the sum of n3 and n4 is 1 to 5, preferably 1 to 3, and $L^x$ is a direct bond or represents a terminal segment of L extending from the carbon atom within L that is bound to $R^3$.

When Z is taken together with $R^2$ or $R^3$ to form a ring, which is generally a cycloalkyl ring that is optionally substituted and/or heteroatom-containing, however, the structures are somewhat different, insofar as the $CY^2$ moiety is then a member of the ring rather than contained within an extending substituent. Here, $R^1$ and $R^3$ are preferably H. An example of such a compound is that represented by the structure of formula (VI)

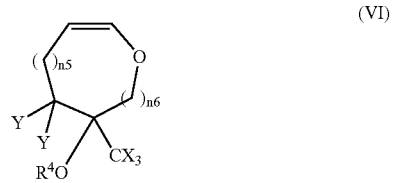

(VI)

wherein X, Y, and $R^4$ are as defined previously, n5 is zero, 1, 2, or 3, n6 is 1, 2, or 3, and the sum of n5 and n6 is generally 1, 2, 3, 4, or 5, more typically 1 or 2. In a variation on this compound, a cyclic fluorinated vinyl ether of the invention may also have the structure of formula (VIA)

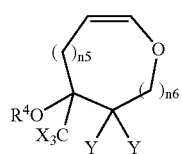
(VIA)

Similarly, when $R^3$ is taken together with Z to form a ring, which is generally a cycloalkyl ring that is optionally substituted and/or heteroatom-containing, $R^1$ and $R^2$ are preferably H. Such a compound may be represented by the structure of formula (VII)

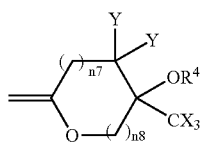
(VII)

wherein n7 is zero, 1, 2, or 3, n8 is 1, 2, or 3, and the sum of n5 and n6 is generally 1, 2, 3, 4, or 5, preferably 2, 3, or 4. In a variation on this compound, a cyclic fluorinated vinyl ether of the invention may also have the structure of formula (VIIA)

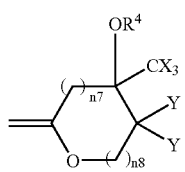
(VIIA)

In all of these molecular structures, i.e., (I) and (III) through (VII), $R^4$ is selected from H, an acid-labile group optionally substituted with one or more fluorine atoms, and an acid-inert moiety optionally substituted with one or more fluorine atoms.

Acid-inert $R^4$ moieties include, by way of example, fluorinated alkyl groups, with fluorinated lower alkyl groups preferred, and fluorinated alkanol groups, including fluorinated lower alkanol groups. Examples of fluorinated lower alkanol groups are -L-C(CX$_3$)(CY$_2$Z)-OH, wherein L, X, Y, and Z are as defined previously. Acid-inert moieties also include alkyl and cycloalkyl groups that do not contain a tertiary attachment point.

Acid-labile $R^4$ moieties include tertiary alkyl, e.g., t-butyl, or a cyclic or alicyclic substituent (generally $C_6$-$C_{12}$) with a tertiary attachment point such as adamantyl, norbornyl, isobornyl, 2-methyl-2-adamantyl, 2-methyl-2-isobornyl, 2-methyl-2-tetracyclododecenyl, 2-methyl-2-dihydrodicyclo-pentadienyl-cyclohexyl, 1-methylcyclohexyl, or 1-methylcyclopentyl (MCP). Acid-labile moieties also include -(Q-CO—O)$_x$—R$^{14}$, -(Q)$_y$—(CO)—O—R$^{15}$, —CR$^{16}$R$^{17}$—O—R$^{18}$, and trialkylsilyl (preferably tri(lower alkyl)silyl), wherein x and y are integers, typically in the range of 1 to 8 inclusive, Q is an alkylene group optionally substituted with one or more fluorine atoms, y is zero (i.e., Q is not present) or 1, $R^{14}$ and $R^{15}$ are optionally substituted hydrocarbyl, typically alkyl or fluorinated alkyl, preferably lower alkyl or fluorinated lower alkyl, $R^{16}$ and $R^{17}$ are H, alkyl (typically lower alkyl), fluoroalkyl (typically lower fluoroalkyl), or alicyclic, or are taken together to form a ring, typically a five- to seven-membered ring, and $R^{18}$ is alkyl (typically lower alkyl), fluoroalkyl (typically lower fluoroalkyl), or alicyclic, or can be taken together with $R^{16}$ or $R^{17}$ to form a ring, e.g., a five- to nine-membered, preferably a five- to seven-membered heterocyclic ring that may or may not contain an additional heteroatom.

Other examples of acid-labile groups are set forth in U.S. Pat. No. 4,491,628 to Ito et al., entitled "Positive- and Negative-Working Resist Compositions with Acid-Generating Photoinitiator and Polymer with Acid Labile Groups Pendant from Polymer Backbone," and in the *Handbook of Microlithography, Micromachining, and Microfabrication*, Vol. 1: *Microlithography*, Ed. P. Raj-Coudhury, p. 321 (1997). Still other suitable acid-labile groups may be found in U.S. Pat. No. 5,679,495 to Yamachika et al. or in the pertinent literature and texts (e.g., Greene et al., Protective Groups in Organic Synthesis, 2$^{nd}$ Ed. (New York: John Wiley & Sons, 1991)).

Exemplary and particularly preferred fluorinated vinyl ethers of formula (I) are VE-PrHFA (1,1,1-trifluoro-2-trifluoromethyl-5-vinyloxy-pentan-2-ol) and VE-NBHFA (1,1,1,3,3,3-hexafluoro-(6- or 5-)vinyloxy-bicyclo[2.2.1]hept-2-ylmethyl)-propan-2-ol):

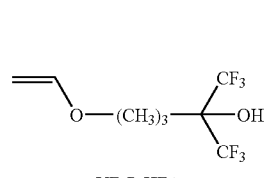
VE-PrHFA

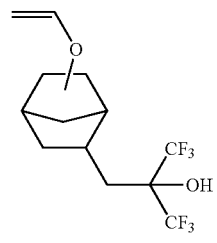
VE-NBHFA

Synthesis of these fluorinated vinyl ethers is described in Examples 1, 2, 3, and 4.

Fluorinated vinyl ethers of the invention may be synthesized from a starting material having the structure of formula (VIII) or (VIIIA)

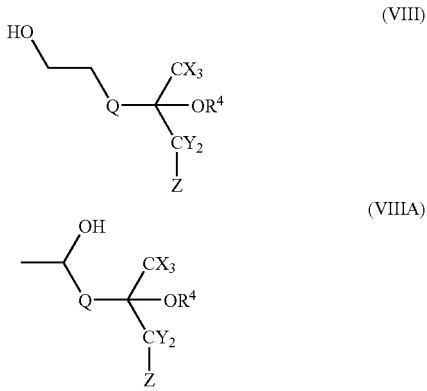

wherein Q is a segment of L, i.e., L is —CH$_2$CH$_2$-Q- in formula (VIII), and is —CH$_2$-Q- in formula (VIIIA). These alcohols may be derived from hydration of the corresponding olefin (IX)

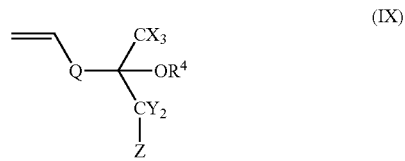

To convert (VIII) or (VIIIA) to a fluorinated vinyl ether of the invention, the compound is transetherified with an appropriately substituted co-reactant in the presence of an Hg or Ir catalyst (see Watanabe et al. (1957) *J. Am. Chem. Soc.* 79:2828 and Okimoto et al. (2002) *J. Am. Chem. Soc.* 124: 1590). With an Hg catalyst, e.g., $Hg(OAc)_2$ (Ac=acetyl), the co-reactant is $CR^1R^2=CR^3(OR^{19})$ wherein $R^1$, $R^2$, and $R^3$ are as defined previously, and $R^{19}$ is lower alkyl, e.g., ethyl. With an Ir catalyst, e.g., $[Ir(COD)Cl]_2$ (COD=cyclooctadiene), the co-reactant is $CR^1R^2=CR^3(OR^{20})$ wherein $R^1$, $R^2$, and $R^3$ are as defined previously, and $R^{20}$ is lower acyl, e.g., acetyl. See Examples 1 through 5. A significant advantage of these syntheses is that the desired product can be synthesized directly from the corresponding diol, i.e., compound (VIII) wherein $R^4$ is H, without having to protect the acidic fluoroalcohol $(-C(CX_3)(CY_2Z)\text{-OH})$ moiety. Of course, other syntheses may also be used to prepare the fluorinated vinyl ethers of the invention, including syntheses that are known or may become known to those of ordinary skill in the art, and/or syntheses that are described in the pertinent texts and literature references.

In another embodiment, a fluorinated copolymer is prepared by copolymerization of at least one fluorinated vinyl ether of the invention, preferably having the structure of formula (I), and at least one monomer having the structure of formula (II)

wherein the substituents are as follows:

$R^5$ is selected from F, lower fluoroalkyl, cyano, —(CO)—O—$R^9$, —(CO)—$NR^{10}R^{11}$, —(CO)—$R^{12}$, and —$S(O)_2$—$OR^{13}$, or is taken together with $R^6$ or $R^8$ to form a ring, generally a five- to nine-membered ring. Preferably, $R^5$ is selected from F, lower fluoroalkyl, and cyano, and more preferably is F, lower fluoroalkyl (e.g., trifluoromethyl) or cyano.

$R^6$, $R^7$, and $R^8$ are independently selected from H, F, lower alkyl, lower fluoroalkyl, cyano, —(CO)—O—$R^9$, —(CO)—$NR^{10}R^{11}$, —(CO)—$R^{12}$, and —$S(O)_2$—$OR^{13}$, and, in addition, $R^7$ may be taken together with $R^6$ or $R^8$ to form a ring, generally a five- to nine-membered ring, typically a five- to seven-membered ring. In the latter case, when $R^7$ is taken together with $R^6$ or $R^8$ to form a ring, the ring is preferably formed through an alkylene linkage that is optionally substituted and/or heteroatom-containing, thus including, for example, lactones and cyclic anhydrides. Monomers containing such rings include, without limitation, maleic anhydride, itaconic anhydride, and α-methylene-γ-butyrolactone.

In the foregoing substituents, $R^9$ is H, an acid-labile moiety optionally substituted with one or more fluorine atoms, or an acid-inert moiety optionally substituted with one or more fluorine atoms, and $R^{10}$, $R^{11}$, $R^{12}$, and $R^{13}$ are independently selected from H, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_3$-$C_{15}$ alicyclic, $C_3$-$C_{15}$ fluoroalicyclic, $C_5$-$C_{14}$ aryl, substituted $C_5$-$C_{14}$ aryl, $C_5$-$C_{14}$ heteroaryl, and substituted $C_5$-$C_{14}$ heteroarylene. In a preferred embodiment, $R^6$ and $R^7$ substituents are both H when $R^5$ is lower fluoroalkyl or cyano, and are both F when $R^5$ is F. In the aforementioned preferred embodiment, $R^8$ is preferably selected from F, cyano, and —(CO)—O—$R^9$, in which $R^9$ is as defined above, with preferred $R^9$ groups selected from acid-labile substituents optionally substituted with a moiety $-L\text{-}C(CX_3)(CY_2Z)\text{-OH}$. Most preferably, $R^9$ is an acid-labile moiety selected from tertiary alkyl substituents and $C_6$-$C_{12}$ alicyclic substituents with a tertiary attachment point.

Accordingly, in a preferred embodiment, the co-monomer has the structure of formula (X)

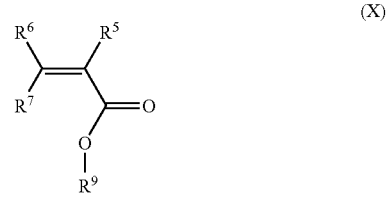

wherein $R^5$ is F, trifluoromethyl, or cyano, and $R^9$ is H, an acid-labile group such as t-butyl or 1-methylcyclopentyl, or is a "fluoroalcohol" substituent such as $-L\text{-}C(CX_3)(CY_2Z)\text{-OH}$, e.g., hexafluoroisopropanol $(-C(CF_3)_2-OH)$. In many preferred compounds, $R^6$ and $R^7$ are both H when $R^5$ is lower fluoroalkyl or cyano, and are both F when $R^5$ is F.

Examples of structure (II) monomers that are preferred include, but are not limited to, the following:

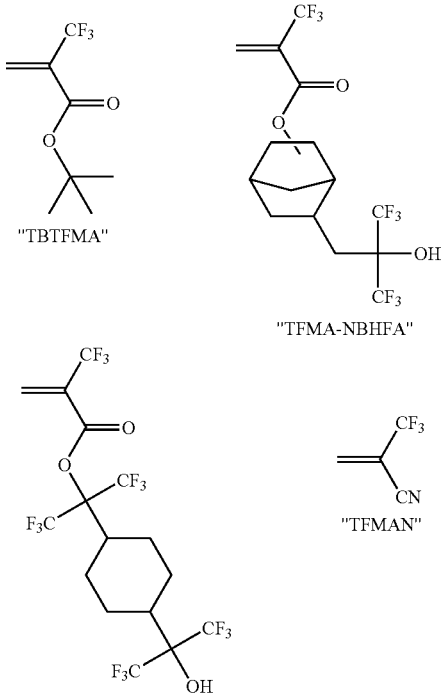

The above abbreviations are as follows: TBTFMA=t-butyl-2-trifluoromethylacrylate; TFMA=α-trifluoromethylacrylate; NBHFA=5-[(1',1',1'-trifluoro-2'-trifluoromethyl-2'-hydroxy)propyl]-2-(or -3-)norbornane; and TFMAN=α-trifluoromethyl acrylonitrile. Other suitable monomers are described in U.S. Pat. No. 6,509,134 to Ito et al., U.S. Patent Publication No. 2002/0102490 to Brock et al., and U.S. Patent Publication No. 2002/0146639 to Brock et al., all assigned to International Business Machines Corporation.

It will also be appreciated that structure (II) comonomers include structurally simple fluorine-containing acid-inert monomers such as $CF_2=CF_2$, $(CF_3)_2C=CF_2$, $(CF_3)_2C=C(CF_3)_2$, $(CF_3)CH=CH(CF_3)$, and α-trifluoromethylstyrene (TFMST).

The copolymer may be prepared from one or more monomers having the structure of formula (I) and from one or more monomers having the structure of formula (II). For example, the copolymer may be prepared from two monomers having the structure of formula (I) and two monomers having the structure of formula (II). Furthermore, the copolymer may also be prepared by using one or more additional monomers not having the structure of formula (I) or formula (II). These monomers will also be addition polymerizable monomers, preferably radically copolymerizable vinyl monomers, and may be advantageously substituted with groups that lower absorbance at 157 nm.

These additional monomers that can be copolymerized along with structure (I) and structure (II) monomers include, without limitation, acrylic acid, methacrylic acid, or trifluoromethacrylic acid, which may be advantageously incorporated to enhance the development and adhesion properties of the resist. The copolymer may also comprise other suitable monomer units such as hydroxystyrene to enhance development and etch resistance, or a silicon-containing monomer unit (e.g., a silicon-containing acrylate, methacrylate or styrene) to enhance oxygen plasma etch resistance for bilayer applications. The additional monomers also include vinyl sulfonates and maleic anhydride. In general, suitable comonomers to be used in addition to those of formulae (I) and (II) include, but are not limited to, the following ethylenically unsaturated polymerizable monomers: acrylic and methacrylic acid esters and amides, including alkyl acrylates, aryl acrylates, alkyl methacrylates and aryl methacrylates (for example, methyl acrylate, methyl methacrylate, n-butyl acrylate, n-butyl methacrylate, t-butyl acrylate, t-butyl methacrylate, 2-ethylhexyl methacrylate, benzyl acrylate and N-phenylacrylamide); vinyl aromatics, including unsubstituted styrene and styrene substituted with one or two lower alkyl, halogen or hydroxyl groups (for example, styrene derivatives such as 4-vinyltoluene, 4-vinylphenol, α-methylstyrene, 2,5-dimethylstyrene, 4-t-butylstyrene and 2-chlorostyrene); butadiene; vinyl acetate; vinyl bromide; vinylidene chloride; fluorinated analogs of any of the foregoing, e.g., fluorinated acrylic and methacrylic acid esters (e.g., fluorinated alkyl acrylates, fluorinated aryl acrylates, fluorinated alkyl methacrylates and fluorinated aryl methacrylates); vinyl sulfonates, maleic anhydride; and others readily apparent to one skilled in the art.

The copolymer formed from structures (I) and (II) above is comprised of monomer units having the structure (XI)

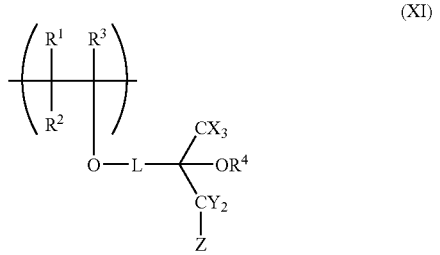

(XI)

and monomer units having the structure (XII)

(XII)

where L, X, Y, Z, and $R^1$ through $R^8$ are as defined previously. The copolymer may also include one or more additional monomer units deriving from the incorporation of additional monomers into the polymerization reaction as described above.

The copolymer may advantageously have molar fractions of the monomer units (XI) and (XII) in the range of approximately 0.1 to 0.9 and 0.9 to 0.1, respectively, with the molar fraction of the additional monomer unit(s) in the range of zero to approximately 0.5.

The copolymers provided herein can be prepared by radical copolymerization, using a suitable free radical initiator. The initiator may be any conventional free radical-generating polymerization initiator. Examples of suitable initiators include peroxides such as O-t-amyl-O-(2-ethylhexyl)monoperoxycarbonate, dipropylperoxydicarbonate, and benzoyl peroxide (BPO), as well as azo compounds such as azobisisobutyronitrile (AIBN), 2,2'-azobis(2-amidino-propane)dihydrochloride, and 2,2'-azobis(isobutyramide)dihydrate. The initiator is generally present in the polymerization mixture in an amount of from about 0.2 to 5% by weight of the monomers. The resulting copolymer typically has a number average molecular weight in the range of approximately 500 to 50,000, generally in the range of approximately 1,000 to 20,000.

III. Resist Compositions

In another embodiment, a photoresist composition is provided that comprises both a copolymer as described in detail above and a photoacid generator, with the copolymer representing up to about 99 wt. % of the solids included in the composition, and the photoacid generator representing approximately 0.5 to 10 wt. % of the solids contained in the composition. Other components and additives (e.g., dissolution modifying additives such as dissolution inhibitors) may also be present. For improved transparency at 157 nm, the dissolution modifying additive is preferably a fluorine-containing material.

The copolymer may be incorporated into the resist composition as is, or in the form of a blend with one or more additional polymers. Any such additional polymers are generally selected to increase transparency at a desired wavelength, e.g., 157 nm or 193 nm, increase dry etch resistance, and/or improve aqueous base development. Additional polymers include, by way of example, norbornene polymers. A preferred group of such polymers are those described in U.S. Ser. No. 10/090,646, cited earlier herein, which are comprised of monomer units having the structure of formula (XIII)

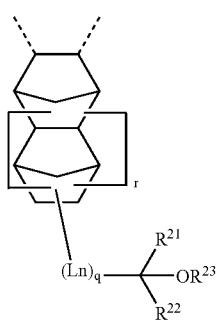

(XIII)

wherein: q is zero or 1; r is zero or 1; Ln is a linking group and is defined as for L; $R^{21}$ is defined as for X; $R^{22}$ is defined as for Y; and $R^{23}$ is defined as for $R^4$. The polymer may be a homopolymer, as in PNBHFA, or it may be a copolymer containing additional types of monomer units, e.g., resulting from polymerization of monomers of formula (II) or other norbornene monomers.

The photoacid generator may be any compound that, upon exposure to radiation, generates a strong acid and is compatible with the other components of the photoresist composition. Examples of preferred photochemical acid generators (PAGs) include, but are not limited to, α-(trifluoromethylsulfonyloxy)-bicyclo[2.2.1]hept-5-ene-2,3-dicarboximide (MDT), onium salts, aromatic diazonium salts, sulfonium salts, diaryliodonium salts and sulfonic acid esters of N-hydroxyamides or N-hydroxyimides, as disclosed in U.S. Pat. No. 4,731,605. Also, a PAG that produces a weaker acid such as the dodecane sulfonate of N-hydroxy-naphthalimide (DDSN) may be used. Combinations of PAGs may be used. Generally, suitable acid generators have high thermal stability (are preferably stable to temperatures greater than 140° C.) so they are not degraded during pre-exposure processing. In addition to MDT and DDSN, suitable sulfonate compounds are sulfonate salts, but other suitable sulfonate PAGs include sulfonated esters and sulfonyloxy ketones. See U.S. Pat. No. 5,344,742 to Sinta et al., and J. Photopolymer Science and Technology, 4:337 (1991), for disclosure of suitable sulfonate PAGs, including benzoin tosylate, t-butylpheny-α-(p-toluenesulfonyloxy)acetate and t-butyl-α-(p-toluenesulfonyloxy)-acetate. Onium salts are also generally preferred acid generators of compositions provided herein. Onium salts that contain weakly nucleophilic anions have been found to be particularly suitable. Examples of such anions are the halogen complex anions of divalent to heptavalent metals or nonmetals, for example, Sb, B, P, and As. Examples of suitable onium salts are aryl-diazonium salts, halonium salts, aromatic sulfonium salts and sulfoxonium salts or selenium salts, (e.g., triarylsulfonium and diaryliodonium hexafluoroantimonates, hexafluoroarsenates, trifluoromethanesulfonates and others). One preferred diaryliodonium salt is iodonium perfluorooctanesulfonate and is disclosed in U.S. Pat. No. 6,165,673 to Breyta et al. Examples of suitable preferred onium salts can be found in U.S. Pat. Nos. 4,442,197, 4,603,101, and 4,624,912. Other useful acid generators include the family of nitrobenzyl esters, and the s-triazine derivatives. Suitable s-triazine acid generators are disclosed, for example, in U.S. Pat. No. 4,189,323.

Still other suitable acid generators include: sulfonyloxynaphthalimides such as N-camphorsulfonyloxynaphthalimide and N-pentafluorophenylsulfonyloxynaphthalimide; ionic iodonium sulfonates, e.g., diaryl iodonium (alkyl or aryl) sulfonate and bis-(di-t-butylphenyl)-iodonium camphanylsulfonate; perfluoroalkanesulfonates, such as perfluoropentanesulfonate, perfluorooctanesulfonate, and perfluoromethanesulfonate; aryl (e.g., phenyl or benzyl)triflates and derivatives and analogs thereof, e.g., triphenylsulfonium triflate or bis-(t-butylphenyl)iodonium triflate; pyrogallol derivatives (e.g., trimesylate of pyrogallol); trifluoromethanesulfonate esters of hydroxyimides; α, α'-bis-sulfonyl-diazomethanes; sulfonate esters of nitro-substituted benzyl alcohols; naphthoquinone-4-diazides; and alkyl disulfones. Other suitable photoacid generators are disclosed in Reichmanis et al. (1991), Chemistry of Materials 3:395, and in U.S. Pat. No. 5,679,495 to Yamachika et al. Additional suitable acid generators useful in conjunction with the compositions and methods provided herein will be known to those skilled in the art and/or are described in the pertinent literature.

With a positive photoresist composition, a dissolution modifying additive, generally although not necessarily a dissolution inhibitor, is included, while with a negative photoresist composition, a crosslinking agent will be present. If dissolution inhibitors and crosslinking agents are present, they will typically represent in the range of about 1 wt. % to 40 wt. %, preferably about 5 wt. % to 30 wt. %, of the total solids.

Suitable dissolution inhibitors will be known to those skilled in the art and/or described in the pertinent literature. Preferred dissolution inhibitors have high solubility in the resist composition and the solvent used to prepare solutions of the resist composition (e.g., propylene glycol methyl ether acetate, or "PGMEA"), exhibit strong dissolution inhibition, have a high exposed dissolution rate, are substantially transparent at the wavelength of interest, may exhibit a moderating influence on $T_g$, strong etch resistance, and display good thermal stability (i.e., stability at temperatures of about 140° C. or greater). Suitable dissolution inhibitors include, but are not limited to, bisphenol A derivatives, e.g., wherein one or both hydroxyl moieties are converted to a t-butoxy substituent or a derivative thereof such as a t-butoxycarbonyl or t-butoxycarbonylmethyl group; fluorinated bisphenol A derivatives such as $CF_3$-bisphenol A-OCH$_2$(CO)—O-tBu (6F-bisphenol A protected with a t-butoxycarbonylmethyl group); normal or branched chain acetal groups such as 1-ethoxyethyl, 1-propoxyethyl, 1-n-butoxyethyl, 1-isobutoxy-ethyl, 1-t-butyloxyethyl, and 1-t-amyloxyethyl groups; and cyclic acetal groups such as tetrahydrofuranyl, tetrahydropyranyl, and 2-methoxytetrahydro-pyranyl groups; androstane-17-alkylcarboxylates and analogs thereof, wherein the 17-alkylcarboxylate at the 17-position is typically lower alkyl. Examples of such compounds include lower alkyl esters of cholic, ursocholic and lithocholic acid, including methyl cholate, methyl lithocholate, methyl ursocholate, t-butyl cholate, t-butyl lithocholate, t-butyl ursocholate, and the like (see, e.g., Allen et al. (1995) J. Photopolym. Sci. Technol., cited supra); hydroxyl-substituted analogs of such compounds (ibid.); and androstane-17-alkylcarboxylates substituted with 1 to 3 $C_1$-$C_4$ fluoroalkyl carbonyloxy substituents, such as t-butyl trifluoroacetyllithocholate (see, e.g., U.S. Pat. No. 5,580,694 to Allen et al.).

Preferred dissolution inhibitors herein are fluoroalcohol-based dissolution inhibitors such as those having the structure (XIV)

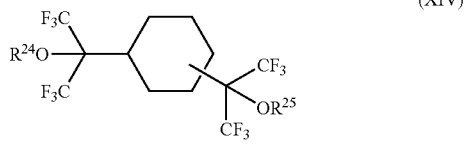

wherein $R^{24}$ and $R^{25}$ are acid-labile groups such as -(Q'—CO—O)$_{x1}$—$R^{26}$, -(Q')$_{y1}$—(CO)—O—$R^{27}$, and —$CR^{28}R^{29}$—O—$R^{30}$ wherein $R^{26}$, $R^{27}$, $R^{28}$, $R^{29}$, and $R^{30}$ are defined as for $R^{14}$, $R^{15}$, $R^{16}$, $R^{17}$, and $R^{18}$, respectively, x1 and y1 are integers in the range of 1 to 8 inclusive, and Q' is defined as for Q.

The crosslinking agent used in the photoresist compositions provided herein may be any suitable crosslinking agent known in the negative photoresist art which is otherwise compatible with the other selected components of the photoresist composition. The crosslinking agents preferably act to crosslink the polymer component in the presence of a generated acid. Preferred crosslinking agents are glycoluril compounds such as tetramethoxymethyl glycoluril, methylpropyltetramethoxymethyl glycoluril, and methylphenyltetramethoxymethyl glycoluril, available under the POWDERLINK trademark. from American Cyanamid Company. Other possible crosslinking agents include 2,6-bis(hydroxymethyl)-p-cresol and analogs and derivatives thereof, such as those found in Japanese Laid-Open Patent Application (Kokai) No. 1-293339, as well as etherified amino resins, for example methylated or butylated melamine resins (N-methoxymethyl- or N-butoxymethyl-melamine respectively) or methylated/butylated glycolurils, for example as can be found in Canadian Patent No. 1 204 547. Combinations of crosslinking agents may be used.

The remainder of the resist composition is composed of a solvent and may additionally, if necessary or desirable, include customary additives such as dyes, sensitizers, additives used as stabilizers and acid-diffusion controlling agents, coating aids such as surfactants or anti-foaming agents, adhesion promoters and plasticizers.

The choice of solvent is governed by many factors not limited to the solubility and miscibility of resist components, the coating process, and safety and environmental regulations. Additionally, inertness to other resist components is desirable. It is also desirable that the solvent possess the appropriate volatility to allow uniform coating of films yet also allow significant reduction or complete removal of residual solvent during the post-application bake process. See, e.g., Introduction to Microlithography, Eds. Thompson et al., cited previously. In addition to the above components, the photoresist compositions provided herein generally include a casting solvent to dissolve the other components so that the overall composition may be applied evenly on the substrate surface to provide a defect-free coating. Where the photoresist composition is used in a multilayer imaging process, the solvent used in the imaging layer photoresist is preferably not a solvent to the underlayer materials, otherwise the unwanted intermixing may occur. The invention is not limited to selection of any particular solvent. Suitable casting solvents may generally be chosen from ether-, ester-, hydroxyl-, and ketone-containing compounds, or mixtures of these compounds. Examples of appropriate solvents include carbon dioxide, cyclopentanone, cyclohexanone, ethyl 3-ethoxypropionate (EEP), a combination of EEP and γ-butyrolactone (GBL), lactate esters such as ethyl lactate, alkylene glycol alkyl ether esters such as PGMEA, alkylene glycol monoalkyl esters such as methyl cellosolve, butyl acetate, and 2-ethoxyethanol. Preferred solvents include ethyl lactate, propylene glycol methyl ether acetate, ethyl 3-ethoxypropionate and their mixtures. The above list of solvents is for illustrative purposes only and should not be viewed as being comprehensive nor should the choice of solvent be viewed as limiting the invention in any way. Those skilled in the art will recognize that any number of solvents or solvent mixtures may be used.

Greater than 50 percent of the total mass of the resist formulation is typically composed of the solvent, preferably greater than 80 percent.

Other customary additives include dyes that may be used to adjust the optical density of the formulated resist and sensitizers which enhance the activity of photoacid generators by absorbing radiation and transferring it to the photoacid generator. Examples include aromatics such as functionalized benzenes, pyridines, pyrimidines, biphenylenes, indenes, naphthalenes, anthracenes, coumarins, anthraquinones, other aromatic ketones, and derivatives and analogs of any of the foregoing.

A wide variety of compounds with varying basicity may be used as stabilizers and acid-diffusion controlling additives. They may include nitrogenous compounds such as aliphatic primary, secondary, and tertiary amines, cyclic amines such as piperidines, pyrimidines, morpholines, aromatic heterocycles such as pyridines, pyrimidines, purines, imines such as diazabicycloundecene, guanidines, imides, amides, and others. Ammonium salts may also be used, including ammonium, primary, secondary, tertiary, and quaternary alkyl- and arylammonium salts of alkoxides including hydroxide, phenolates, carboxylates, aryl and alkyl sulfonates, sulfonamides, and others. Other cationic nitrogenous compounds including pyridinium salts and salts of other heterocyclic nitrogenous compounds with anions such as alkoxides including hydroxide, phenolates, carboxylates, aryl and alkyl sulfonates, sulfonamides, and the like may also be employed. Surfactants may be used to improve coating uniformity, and include a wide variety of ionic and non-ionic, monomeric, oligomeric, and polymeric species. Likewise, a wide variety of anti-foaming agents may be employed to suppress coating defects. Adhesion promoters may be used as well; again, a wide variety of compounds may be employed to serve this function. A wide variety of monomeric, oligomeric, and polymeric plasticizers such as oligo- and polyethyleneglycol ethers, cycloaliphatic esters, and non-acid reactive steroidally derived materials may be used as plasticizers, if desired. However, neither the classes of compounds nor the specific compounds mentioned above are intended to be comprehensive and/or limiting. One versed in the art will recognize the wide spectrum of commercially available products that may be used to carry out the types of functions that these customary additives perform.

Typically, the sum of all customary additives will comprise less than 20 percent of the solids included in the resist formulation, preferably, less than 5 percent.

IV. Use in Generation of Resist Images on a Substrate

The present invention also relates to a process for generating a resist image on a substrate comprising the steps of: (a) coating a substrate with a film comprising a resist composition provided herein; (b) imagewise exposing the film to radiation; and (c) developing the image. The first step involves coating the substrate with a film comprising the resist composition dissolved in a suitable solvent. Suitable substrates are ceramic, metallic or semiconductive, and preferred substrates are silicon-containing, including, for example, silicon dioxide, silicon nitride, and silicon oxynitride. The substrate may or may not be coated with an organic anti-reflective layer prior to deposition of the resist composition. Alternatively, a bilayer resist may be employed wherein a resist composition provided herein forms an upper resist layer (i.e., the imaging layer), and the underlayer is comprised of a material that is highly absorbing at the imaging wavelength and compatible with the imaging layer. Conventional underlayers include diazonaphthoquinone (DNQ)/novolak resist material.

Preferably, the surface of the substrate is cleaned by standard procedures before the film is deposited thereon. Suitable solvents for the composition are as described in the preceding section, and include, for example, cyclohexanone, ethyl lactate, and propylene glycol methyl ether acetate. The film can be coated on the substrate using art-known techniques such as spin or spray coating, or doctor blading. Preferably, before the film has been exposed to radiation, the film is heated to an elevated temperature of about 90-150∀ C. for a short period of time, typically on the order of about 1 minute. The dried film has a thickness of about 0.02 to 5.0 microns, preferably about 0.05 to 2.5 microns, and most preferably about 0.10 to 1.0 microns. The radiation may be ultraviolet, electron beam or x-ray. Ultraviolet radiation is preferred, particularly deep ultraviolet radiation having a wavelength of less than about 250 nm, e.g., 157 nm using an $F_2$ excimer laser. The radiation is absorbed by the radiation-sensitive acid generator to generate free acid, which with heating (generally to a temperature of about 90-150° C. for a short period of time, on the order of about 1 minute) causes cleavage of the acid-labile pendant groups and formation of the corresponding acid. It will be appreciated by those skilled in the art that the aforementioned description applies to a positive resist, and with a negative resist the exposed regions would typically be crosslinked by acid.

The third step involves development of the image with a suitable solvent. Suitable solvents include an aqueous base, preferably an aqueous base without metal ions such as the industry standard developer tetramethylammonium hydroxide or choline. Other solvents may include organic solvents or carbon dioxide (in the liquid or supercritical state), as disclosed in U.S. Pat. No. 6,665,527 to Allen et al. Because the copolymer of the resist composition is substantially transparent at 157 nm, the resist composition is uniquely suitable for use at that wavelength. However, the resist may also be used with wavelengths of 193 nm, 248 nm, or with EUV (e.g., at 13 nm) electron beam or x-ray radiation.

The pattern from the resist structure may then be transferred to the material of the underlying substrate. Typically, the transfer is achieved by reactive ion etching or some other etching technique. Thus, the compositions provided herein and resulting resist structures can be used to create patterned material layer structures such as metal wiring lines, holes for contacts or vias, insulation sections (e.g., damascene trenches or shallow trench isolation), trenches for capacitor structures, etc. as might be used in the design of integrated circuit devices. Accordingly, the processes for making these features involves, after development with a suitable developer as above, etching the layer(s) underlying the resist layer at spaces in the pattern whereby a patterned material layer or substrate section is formed, and removing any remaining resist from the substrate. In some instances, a hard mask may be used below the resist layer to facilitate transfer of the pattern to a further underlying material layer or section. In the manufacture of integrated circuits, circuit patterns can be formed in the exposed areas after resist development by coating the substrate with a conductive material, e.g., a metallic material, using known techniques such as evaporation, sputtering, plating, chemical vapor deposition, or laser-induced deposition. Dielectric materials may also be deposited by similar means during the process of making circuits. Inorganic ions such as boron, phosphorous, or arsenic can be implanted in the substrate in the process for making p-doped or n-doped circuit transistors. Examples of such processes are disclosed in U.S. Pat. Nos. 4,855,017, 5,362,663, 5,429,710, 5,562,801, 5,618,751, 5,744,376, 5,801,094, and 5,821,469. Other examples of pattern transfer processes are described in Chapters 12 and 13 of Moreau, *Semiconductor Lithography, Principles, Practices, and Materials* (Plenum Press, 1988). It should be understood that the invention is not limited to any specific lithographic technique or device structure.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

Experimental:

$^1$H and $^{13}$C NMR spectra were obtained at room temperature on an Avance 400 spectrometer. Quantitative $^{13}$C NMR was run at room temperature in acetone-$d_6$ in an inverse-gated $^1$H-decoupled mode using Cr(acac)$_3$ as a relaxation agent on an Avance 400 spectrometer. For polymer composition analysis $^{19}$F NMR (379 MHz) spectra were also obtained using a Bruker Avance 400 spectrometer. Thermo-gravimetric analysis (TGA) was performed at a heating rate of 5° C./min in $N_2$ on a TA Instrument Hi-Res TGA 2950 Thermogravimetric Analyzer. Differential scanning calorimetry (DSC) was performed at a heating rate of 10° C./min on a TA Instruments DSC 2920 modulated differential scanning calorimeter. Molecular weights of the polymers were measured in tetrahydrofuran (THF) on a Waters Model 150 chromatograph relative to polystyrene standards. IR spectra were recorded on a Nicolet 510 FT-IR spectrometer on a film cast on a KBr plate. UV measurements at 157 nm were performed using a Varian Cary Model 400 spectrometer on multiple thickness on $CaF_2$ discs. Film thickness was measured on a Tencor alpha-step 2000. A quartz crystal microbalance (QCM) was used to study the dissolution kinetics of the copolymer films in an aqueous tetramethylammonium hydroxide (TMAH) solution (CD-26). Contact angles were measured on an AST Products VCA 2500XE video contact angle system using 2 µL of filtered deionized water.

Unless otherwise indicated, all reagents were obtained commercially or synthesized according to known methods. TBTFMA, TFMAN, and TFMA-NBHFA were synthesized as described in U.S. Pat. No. 6,509,134 to Ito et al., U.S. Patent Publication No. 2002/0102490 to Brock et al., and U.S. Patent Publication No. 2002/0146639 to Brock et al., all assigned to International Business Machines Corporation.

EXAMPLE 1

Synthesis of 1,1,1-trifluoro-2-trifluoromethyl-5-vinyloxy-pentan-2-ol (VE-PrHFA)

(a) Preparation of 1,1,1-trifluoro-2-trifluoromethyl-2,5-pentanediol and 1,1,1-trifluoro-2-trifluoromethyl-2,4-pentanediol: To a 3-necked, 3-L round bottomed flask equipped with an overhead stirrer, digital thermometer and a 1-L constant-pressure addition funnel with a nitrogen inlet was added 974 mL (1.95 mol) of borane-dimethylsulfide complex (2.0 M in tetrahydrofuran). The addition funnel was charged with a solution of 353 g (1.7 mol) of 1,1,1-trifluoro-2-trifluoromethyl-4-penten-2-ol in 400 mL of anhydrous tetrahydrofuran. The flask was cooled and the olefin was added slowly with stirring while maintaining a temperature below 15° C. The mixture was stirred at room temperature for two days after which time it was recooled and 750 mL (2.25 mol) of 3M NaOH was added carefully. The reaction mixture was reduced in volume on a rotary evaporator and subsequently co-evaporated with two 500 mL portions of diethyl ether. The resulting heavy oil was taken up in 300 mL of THF and the solution transferred to a 1-L 3-necked round-bottomed flask equipped with a 250-mL addition funnel, a digital thermometer and a magnetic stir bar. The addition funnel was charged with 250 mL of 30% hydrogen peroxide. The flask was cooled and the hydrogen peroxide added slowly with stirring. After stirring overnight at room temperature, the solution was diluted with 1 L of diethyl ether and adjusted to pH 6 (wet litmus) with 5% HCl. The ether layer was separated and the aqueous layer was extracted with 2×500 mL of ether. The combined organic phases were washed with 2×500 mL of saturated ammonium chloride and brine, dried over $MgSO_4$ and evaporated to a crude yield of 379 g of a 45:55 (2°:1°) mixture of the two diols. The diols were separated by distillation through a 12" Vigreux, bp 47° C. at 1.0 mm Hg (2° alcohol) and bp 55° C. at 1.0 mm Hg (1° alcohol). The 1° alcohol is a viscous oil while the 2° alcohol is a low melting solid.

(b) Synthesis of 1,1,1-trifluoro-2-trifluoromethyl-5-vinyloxy-pentan-2-ol (VE-PrHFA) with chloro-1,5-cyclooctadiene iridium(I) dimer (Scheme 1)

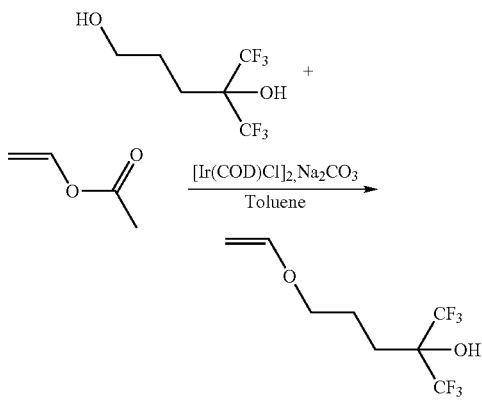

1,1,1-Trifluoro-2-trifluoromethyl-2,5-pentanediol (11.3 g, 50 mmol), toluene (50 mL), sodium carbonate (10.6 g, 100 mmol), chloro-1,5-cyclooctadiene iridium(I) dimer (0.34 g, 0.5 mmol), vinyl acetate(14 mL, 150 mmol) were placed in a dry 250 mL round-bottom flask equipped with a stir bar, condenser, and nitrogen inlet. The reaction mixture was heated to 100° C. and stirred for 3 hours, after which time it was cooled to room temperature. Diethyl ether (50 mL) was added to quench the reaction. After adding charcoal, the mixture was stirred for 1 hr and filtered with Celite 521. Diethyl ether, excess vinyl acetate, and solvent were distilled off under reduced pressure. The degree of the transetherification of the primary diol was found to be 52% by GC. Vacuum distillation (68-70° C., 15 mm Hg) afforded 3.13 g (25%) of colorless liquid.

EXAMPLE 2

Alternative Synthesis of VE-PrHFA Using Mercuric Acetate

To a 500-mL, 3-necked round bottomed flask equipped with a nitrogen inlet, digital thermometer and magnetic stir bar was added 45 g (0.2 mol) of 1,1,1-trifluoro-2-trifluoromethyl-2,5-pentanediol (prepared in part (a) of Example 1), 300 g (4.2 mol) of ethyl vinyl ether and 2.5 g (0.008 mol) of mercuric acetate and the solution stirred at room temperature for 2 days. The mixture was evaporated on a rotary evaporator, diluted with 500 mL of diethyl ether and washed sequentially with saturated sodium bicarbonate, water and brine. After stirring over anhydrous magnesium sulfate overnight, the suspension was filtered, the solvent removed on a rotary evaporator and the resulting oil filtered through a plug of silica gel as a hexane solution. Hexane was evaporated and the resulting oil distilled four times at 70° C. @ 15 mmHg. The best fractions were pooled to yield 17.5 g (35%) of the product as a clear, colorless oil.

EXAMPLE 3

Synthesis of 1,1,1,3,3,3-Hexafluoro-(6- or 5-)vinyloxy-bicyclo[2.2.1]hept-2-ylmethyl)-propan-2-ol (VE-NBHFA)

(a) Preparation of 2-hydroxy-5-[(1',1',1'-trifluoro-2'-trifluoromethyl-2'-hydroxy)propyl]norbornane: To a 3-necked, 500-mL round bottomed flask equipped with a condenser (nitrogen inlet), digital thermometer and magnetic stir bar was added 173.2 g (0.63 mol) of 5-[(1',1',1'-trifluoro-2'-trifluoromethyl-2'-hydroxy)propyl]-2-norbornene and 100 g (1.9 mol) of formic acid (88%) and the mixture heated at 100° C. under nitrogen overnight. The resulting yellow solution was evaporated on a rotary evaporator leaving a thick yellow oil to which was added 120 mL of concentrated ammonium hydroxide (28%) and the mixture heated with stirring at 60° C. overnight. After cooling, the layers were separated and the lower layer was diluted with 500 mL of diethyl ether and washed sequentially with 5% (v/v) HCl (2×250 mL), water (2×200 mL) and brine. The ether solution was dried over $MgSO_4$, evaporated and distilled at 92° C. at 0.8 mm Hg to yield 156 g (84%) of the product as a clear, colorless oil.

(b) Synthesis of VE-NBHFA using mercuric acetate: In a dry 250 mL round-bottom flask equipped with a stir bar, condenser, and nitrogen inlet 2-hydroxy-5-[(1',1',1'-trifluoro-2'-trifluoromethyl-2'-hydroxy)propyl]norbornane (20.5 g, 70 mmol), ethyl vinyl ether (140 mL), mercuric acetate (1.5 g, 4.7 mmol), and triethylamine (1.3 mL, 9.4 mmol) were placed. The reaction mixture was heated to 50° C. and stirred for 53 hrs (26 hrs sufficient by GC). The mixture was then cooled to room temperature and poured into a 500 mL separatory funnel containing brine. The resulting mixture was extracted four times with diethyl ether. The combined organic extracts were dried over $MgSO_4$ and the solvent was removed by distillation under reduced pressure. Vacuum distillation (87-88° C., 7 mmHg) (sodium bicarbonate, 70 mmol was added to batch to prevent oligomerization) afforded 8.2 g of colorless liquid.

EXAMPLE 4

Scaled-Up Synthesis of VE-NBHFA

To a 1-L, 3-necked round bottomed flask equipped with a nitrogen inlet, digital thermometer and magnetic stir bar was added 100 g (0.34 mol) of 2-hydroxy-5-[(1',1',1'-trifluoro-2'-trifluoromethyl-2'-hydroxy)propyl]norbornane (prepared in part (a) of Example 3), 400 g (5.5 mol) of ethyl vinyl ether and 3.2 g (0.01 mol) of mercuric acetate and the solution stirred at room temperature for 2 days. The mixture was evaporated on a rotary evaporator, diluted with 500 mL of diethyl ether and washed sequentially with saturated sodium bicarbonate, water and brine. After stirring over anhydrous magnesium sulfate overnight, the suspension was filtered, the solvent removed on a rotary evaporator and the resulting oil distilled twice from solid sodium bicarbonate at 96° C. @ 0.5 mmHg. The best fractions were pooled to yield 54 g (50%) of the product as a clear, colorless oil.

EXAMPLE 5

Synthesis of TBTFMA/VE-PrHFA Copolymer

Radical copolymerization of t-butyl 2-trifluoromethylacrylate (TBTFMA, 0.55 g, 2.8 mmol) with VE-PrHFA (0.71 g, 2.8 mmol) was carried out at 60° C. for 14 hrs in $N_2$ after deaeration, using AIBN (0.04 g, 0.2 mmol: 4.0 mol %) as the initiator in ethyl acetate (5.6 mL). The copolymer was purified by repeated precipitation in hexane and dried in a vacuum oven at 60° C. overnight (Yield 61%). The composition of the resulting copolymer was found to be TBTFMA/VE-PrHFA=68/32 by $^{19}F$ NMR ($M_n$=10645, $M_w$=16616, $M_w/M_n$=1.53, $T_g$=89° C.).

EXAMPLE 6

TBTFMA/VE-NBHFA Copolymer

Radical copolymerization of TBTFMA (7.8590 g, 40 mmol) with VE-NBHFA (12.7388 g, 40 mmol) was carried out at 60° C. for 19 hrs in $N_2$ after deaeration, using AIBN (0.05256 g, 3.2 mmol: 4.0 mol %) as the initiator in bulk. The mixture solidified in 30 min. The copolymer was purified by repeating precipitation twice in hexanes and dried in a vacuum oven at room temperature overnight (Yield>41%). The composition of the resulting copolymer was TBTFMANE-NBHFA=63/37 by $^{19}F$-NMR ($M_n$=8943, $M_w$=17169, $M_w/M_n$=1.92, $T_g$=124° C.).

EXAMPLE 7

TFMA-NBHFA/VE-PrHFA Copolymer

Radical copolymerization of TFMA-NBHFA (4.1872 g, 10 mmol; TFMA=α-trifluoromethylacrylate) with VE-PrHFA (2.5298 g, 10 mmol) was carried out at 80° C. for 24 hrs in $N_2$ after deaeration, using AIBN (01325 g, 4.0 mol %) as the initiator in ethyl acetate (EtOAc) (60 g). The copolymer was purified by repeated precipitation in hexanes and dried in a vacuum oven at room temperature overnight (Yield>51%). The composition of the resulting copolymer was determined to be TFMA-NBHFA/VE-PrHFA=64/36 by $^{19}F$ and $^{13}C$ NMR ($M_n$=17690, $M_w$=32149, $M_w/M_n$=1.82, $T_g$=76° C.).

EXAMPLE 8

TFMA-NBHFA/VE-NBHFA Copolymer

Radical copolymerization of TFMA-NBHFA (4.1977 g, 10 mmol) with VE-NBHFA (3.200 g, 10 mmol) was carried out at 60° C. for 24 hrs in $N_2$ after deaeration, using AIBN (0.1346 g, 4.0 mol %) as the initiator in EtOAc (5.015 g). The copolymer was purified by 2× precipitation in hexane and dried in a vacuum oven at room temperature overnight (Yield>62%). The composition of the copolymer was TFMA-NBHFA/VE-NBHFA=61/39 by $^{19}F$ NMR ($M_n$=5609, $M_w$=7864, $M_w/M_n$=1.40, $T_g$=1 25° C.).

EXAMPLE 9

TBTFMA/TFMA-NBHFA/VE-PrHFA Terpolymer

Radical terpolymerization of TBTFMA (1.9645 g, 10 mmol), TFMA-NBHFA (2.0846 g, 5 mmol), and VE-PrHFA (2.5236 g, 10 mmol) was carried out at 60° C. for 21 hrs in $N_2$ after deaeration, using AIBN (0.1640 g, 4.0 mol %) as the initiator in EtOAc (1.00 g). The copolymer was purified by 3× precipitation in hexanes and dried in a vacuum oven at room temperature overnight (Yield>83%). The composition of the terpolymer was determined to be TBTFMA/TFMA-NBHFA/VE-PrHFA=41/23/36 by $^{13}C$ NMR ($M_n$=58674, $M_w$=439974, $T_g$=71° C.).

EXAMPLE 10

TBTFMA/TFMA-NBHFA/VE-NBHFA Terpolymer

Radical terpolymerization of TBTFMA (1.9654 g, 10 mmol), TFMA-NBHFA (2.0942 g, 5 mmol), and VE-NBHFA (3.1889 g, 10 mmol) was carried out at 60° C. for 24 hrs in $N_2$ after deaeration, using AIBN (0.1648 g, 4.0 mol %) as the initiator in EtOAc (3.0 g). The terpolymer was purified by repeating precipitation twice in hexanes and dried in a vacuum oven at room temperature overnight (Yield>56%). The composition of the terpolymer was determined by $^{13}C$ NMR to be 50/24/26 ($M_n$=4416, $M_w$=6605, $M_w/M_n$=0.37, $T_g$=123° C.).

EXAMPLE 11

Resist Formulation Prepared with TBTFMA/TFMA-NBHFA/VE-NBHFA Terpolymer

Figure 1B:
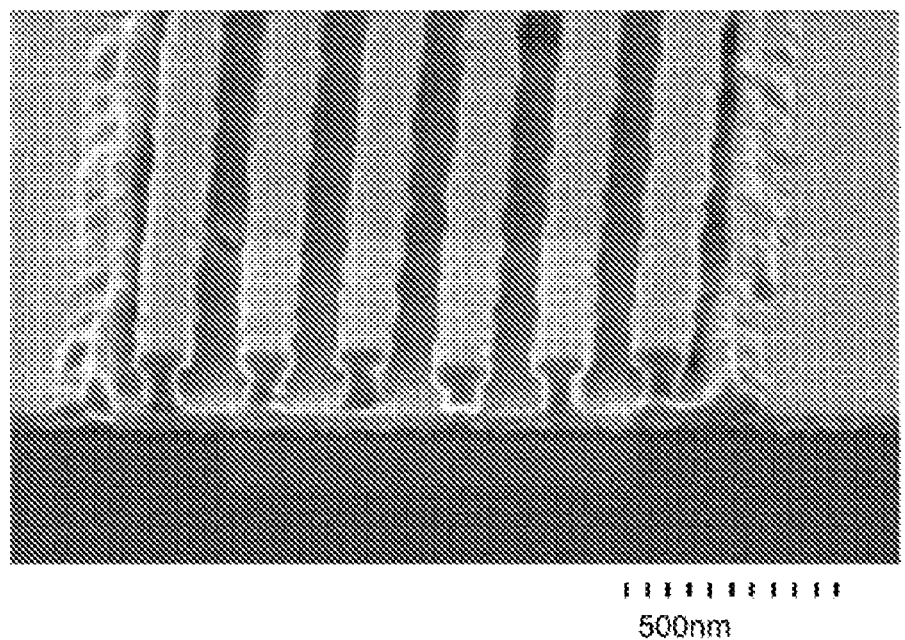
Figure 2A:
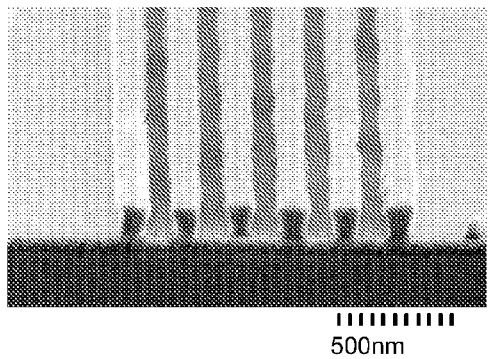
FIGS. 2A, 2B, 2C, and 2D are SEM photos of a patterned resist prepared using a polymer blend of the invention, as described in Example 12 (using 193 nm exposure).
Figure 2B:
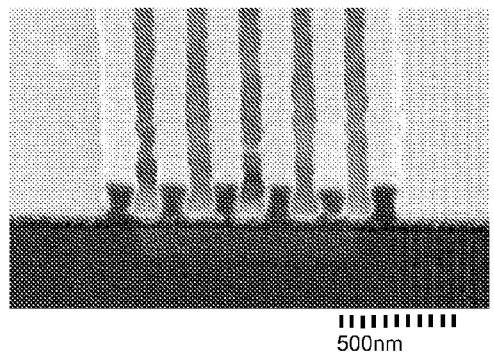
Figure 2C:
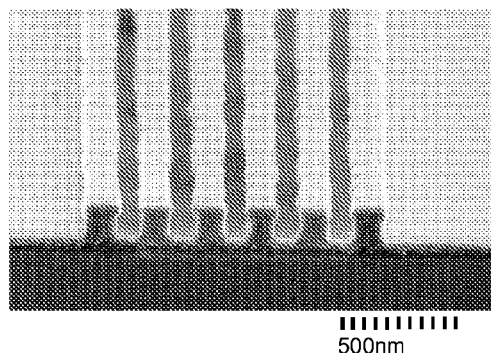
Figure 2D:
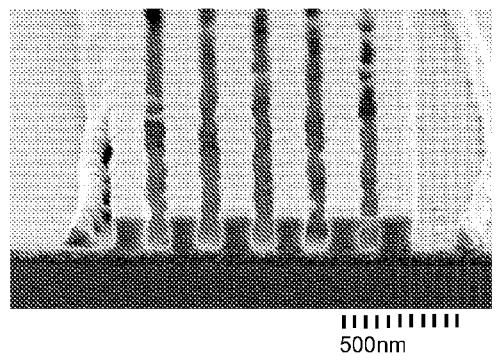

A chemical amplification resist was formulated from the terpolymer of Example 10 (TBTFMA/TFMA-NBHFA/VE-NBHFA, OD of 2.1/μm at 157 nm) by adding the polymer to propylene glycol methyl ether acetate (PGMEA), followed by bis-(t-butylphenyl)iodonium perfluorooctanesulfonate (IPFOS) (4 wt. %) and tetrabutylammonium hydroxide (TBAH, 0.2 wt. %). The resist was spin-coated onto a silicon wafer or onto an antireflective coating (e.g., AR19), soft-baked at 130° C. for 60 seconds, exposed to 193 nm radiation using an ISI 193 Mini-stepper and a chrome-on-glass mask, post-exposure baked at 140° C. for 60 seconds, and then developed with a 0.26 N TMAH aqueous solution. FIGS. 1A and 1B are SEM photos illustrating the excellent resolution obtained, 130 nm lines/space (L/S) and 120 nm L/S patterns printed with the resist formulation.

EXAMPLE 12

Resist Formulation Prepared with a Blend of Poly(TBTFMA$_{60}$/VE-NBHFA$_{40}$) Copolymer and NBHFA Homopolymer (PNBHFA)

Figure 3:
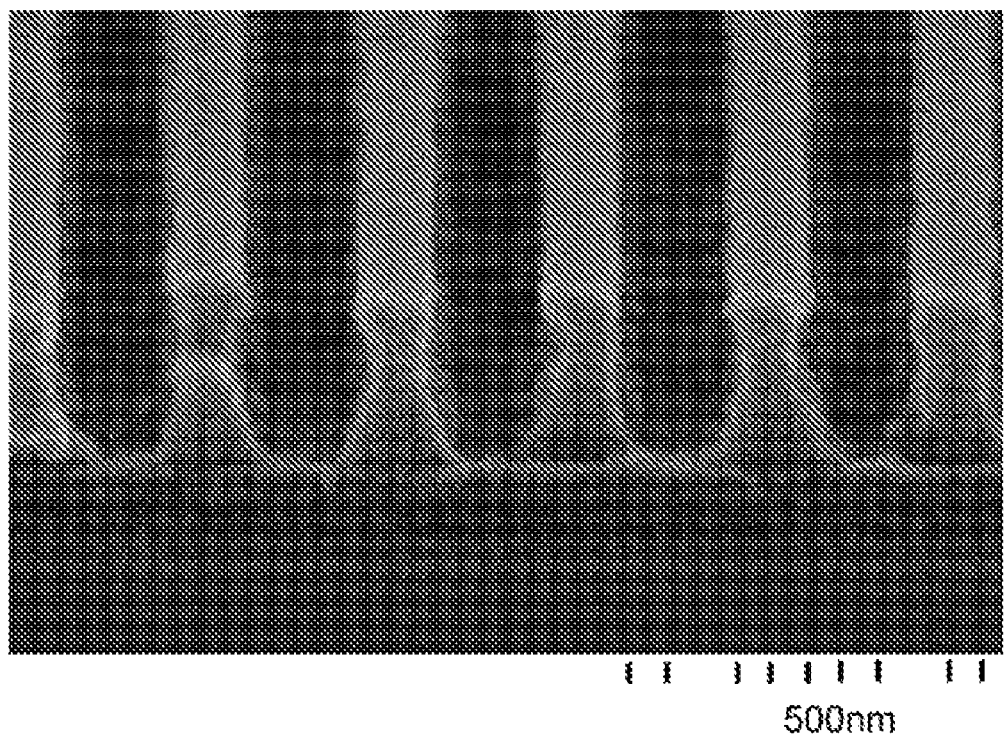
FIG. 3 is an SEM photo of an analogous patterned blend resist, also prepared as described in Example 12, but using a 157 nm exposure.

A chemical amplification resist was formulated from a blend of poly(TBTFMA$_{60}$/VE-NBHFA$_{40}$) (as may be prepared according to Example 6) and PNBHFA by mixing the polymers at a 1:1 ratio in propylene glycol methyl ether acetate (PGMEA), followed by addition of IPFOS (4 wt. %) and TBAH (0.2 wt. %). The resist was spin-coated onto silicon wafers, soft-baked at 130° C. for 60 seconds, exposed to 193 nm radiation using a chrome-on-glass mask, post-exposure baked at 140° C. for 60 seconds, and then developed with a 0.26 N TMAH aqueous solution. FIGS. 2A, 2B, 2C, and 2D are SEM photos showing the dense (120 nm L/S) patterns printed with the resist formulation (corresponding to 30.0, 29.4, 28.8, and 28.2 mJ/cm$^2$). FIG. 3 is an SEM photo of an analogous patterned blend resist prepared as above but employing a 157 nm exposure step (using an Exitech 157 nm tool, NA=0.85), and is also indicative of superior resolution.

The results obtained contrasted markedly with earlier formulations based on trifluoromethylacrylate copolymers and on blends of such copolymers with PNBHFA, which exhibited significant adhesion failure on bare Si. In addition, only the aforementioned blends enabled effective printing.

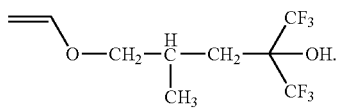

We claim:
1. A fluorinated vinyl ether having the structure